(12) United States Patent
Novac

(10) Patent No.: US 10,429,334 B2
(45) Date of Patent: Oct. 1, 2019

(54) HUMIDITY SENSOR WITH HEAT MODULE

(71) Applicant: EM Microelectronic-Marin SA, Marin (CH)

(72) Inventor: Pinchas Novac, Neuchatel (CH)

(73) Assignee: EM Microelectronic-Marin SA, Marin (CH)

( * ) Notice: Subject to any disclaimer, the term of this patent is extended or adjusted under 35 U.S.C. 154(b) by 96 days.

(21) Appl. No.: 15/553,402

(22) PCT Filed: Feb. 24, 2016

(86) PCT No.: PCT/EP2016/053887
§ 371 (c)(1),
(2) Date: Aug. 24, 2017

(87) PCT Pub. No.: WO2016/135206
PCT Pub. Date: Sep. 1, 2016

(65) Prior Publication Data
US 2018/0074003 A1    Mar. 15, 2018

(30) Foreign Application Priority Data
Feb. 27, 2015 (EP) .................................. 15156949

(51) Int. Cl.
*G01N 27/22* (2006.01)
*G01N 27/12* (2006.01)

(52) U.S. Cl.
CPC ......... *G01N 27/223* (2013.01); *G01N 27/121* (2013.01)

(58) Field of Classification Search
CPC .......................... G01N 27/223; G01N 27/121
See application file for complete search history.

(56) References Cited

U.S. PATENT DOCUMENTS

| | | | | |
|---|---|---|---|---|
| 4,313,338 A | * | 2/1982 | Abe | G01N 27/12 338/34 |
| 5,144,341 A | * | 9/1992 | El Haten | B41J 2/04541 347/12 |
| 5,291,051 A | * | 3/1994 | Hoang | H01L 27/0251 257/355 |
| 6,276,192 B1 | | 8/2001 | Sim et al. | |
| 6,674,185 B2 | * | 1/2004 | Mizuta | G01K 15/00 307/651 |

(Continued)

OTHER PUBLICATIONS

International Search Report dated May 3, 2016 in PCT/EP2016/053887 filed Feb. 24, 2016.

(Continued)

*Primary Examiner* — Walter L Lindsay, Jr.
*Assistant Examiner* — Milton Gonzalez
(74) *Attorney, Agent, or Firm* — Oblon, McClelland, Maier & Neustadt, L.L.P.

(57) ABSTRACT

A humidity sensor is provided, including a silicon base plate on which several intermetallic dielectric layers, each of which is provided with a metallic zone, and a metal layer are disposed, wherein the metal layer is etched to form two electrodes, each including an armature provided with a plurality of arms, wherein each armature is mounted so that the arms are interlaced to have arms positioned to face one another. The sensor also includes a temperature module or a heating module.

6 Claims, 3 Drawing Sheets

(56) References Cited

U.S. PATENT DOCUMENTS

| | | |
|---|---|---|
| 7,554,134 B2 * | 6/2009 | Cummins ............ G01N 27/223 257/252 |
| 2005/0218465 A1 | 10/2005 | Cummins |
| 2007/0131020 A1 | 6/2007 | Itakura et al. |
| 2009/0273009 A1 | 11/2009 | Cummins |
| 2011/0089439 A1 | 4/2011 | Cummins |
| 2011/0089472 A1 | 4/2011 | Cummins |
| 2011/0098937 A1 | 4/2011 | Cummins |
| 2012/0256236 A1 | 10/2012 | Cummins |
| 2015/0316498 A1 | 11/2015 | Cummins |

OTHER PUBLICATIONS

Tuthill, Mike, "A Switched Current, Switched Capacitor Temperature Sensor in 0.6u CMOS," Solid-State Circuits Conference, 1997, ESSCIRC '97, Proceedings of the $2^{rd}$ European, Sep. 1997, XP055207292, 4 pages.

Gu, Lei et al., "A novel capacitive-type humidity sensor using CMOS fabrication technology," Sensors and Actuators B: Chemical: International Journal Devoted to Research and Development of Physical and Chemical Transducers, vol. 99, May 2004, XP004505806, pp. 491-498.

* cited by examiner

HUMIDITY SENSOR WITH HEAT MODULE

CROSS REFERENCE TO RELATED APPLICATION

This application is a U.S. national phase application under 35 U.S.C. § 371 of PCT/EP2016/053887, filed on Feb. 24, 2016, and claims the benefit of priority under 35 U.S.C. § 119 from prior EP Application No. 15156949.8, filed on Feb. 27, 2015, the entire contents of each of which are incorporated herein by reference.

The present invention relates to a humidity sensor comprising a silicon base plate, on which at least a plurality of intermetallic dielectric layers, each of which provided with a metallic zone, and a metal layer are arranged, wherein said metal layer is etched to form two electrodes, each comprising an armature provided with a multiplicity of arms, wherein these armatures are mounted so that the arms of each armature are interlaced to have arms positioned to face one another.

PRIOR ART

Humidity sensors for electronic circuits are known. Such a humidity sensor is a humidity sensor with interdigitated combs.

Such a sensor is composed of a silicon wafer base, on which at least one inter-level dielectric (ILD) layer is positioned and on this inter-level layer a plurality of intermetallic dielectric (IMD) layers are positioned. These layers, preferably three in number, are superposed and each comprise metallic zones for electrical conduction.

On top of these intermetallic dielectric layers a conductive layer serving for the interdigitated comb is formed, wherein this layer may be made from aluminium. This aluminium layer is then etched to form said comb. Once the comb has been formed, the whole assembly is covered with a passivation layer.

This etched plate is then stored, then used in a second phase of production, during which it is prepared for use. This second phase of production consists of an opening step, during which the passivation layer is etched at the level of the comb and at the level of the contact areas. This etching step of the passivation allows etching of the passivation layer located between the different branches of the comb.

Once this step has ended, a protection layer is deposited to protect the aluminium against corrosion and this layer can be an oxynitride layer.

The last step consists of depositing a polyimide layer to protect the whole assembly.

However, this construction poses disadvantages. A first disadvantage results from this sensor being produced in two phases. The fact of having two distinct phases for the production of the sensor actually imposes the presence of additional thermal cycles. These additional thermal cycles cause additional thermal stresses to appear on the plate and the interdigitated comb that can damage said humidity sensor and/or any other circuitry implemented on the same substrate.

A second disadvantage results from the etching during the second phase. In fact, parasitic capacitances occur during the second phase in which the passivation layer is etched. These parasitic capacitances come from etching that is not perfect, i.e. in which the flanks are not perfectly straight. Consequently, residues of the passivation layer are present causing these parasitic capacitances to appear.

Moreover, it must be noted that humidity sensors are sensitive to temperature. This sensitivity to temperature causes a drift in measurements depending on the temperature, so that at a constant humidity rate a temperature variation will influence the output signal supplied by the sensor.

Also known is document US 2005/0218465, which describes a sensing circuit comprising a silicon base plate, on which a sensor is arranged at the level thereof. Three interconnect layers of porous silicon dioxide with a low dielectric constant are deposited on this base plate. Two other interconnect levels are then arranged and these two levels are made from non-porous silicon dioxide. On the last level a metal layer is deposited, then etched to form two electrodes, each comprising an armature provided with a multiplicity of arms, wherein these armatures are mounted so that the arms of each armature are interlaced to have arms positioned to face one another, and the whole assembly forms a humidity sensor.

It is known in this configuration to have a heating element arranged at the level of the last interconnect layer, i.e. below the humidity sensor. This arrangement has the disadvantage of being located just below the sensor and therefore of not allowing an optimum transmission of heat.

Moreover, this sensing circuit is distinguished by the addition of a thin metal layer associated with a thin oxide layer located between the two last interconnect levels allowing the formation of a MIM capacitor. These thin layer components require another technology to be utilised. This technology requires a production process that is a variant of the standard CMOS process, which renders the production of the sensing circuit more complex and more costly.

SUMMARY OF THE INVENTION

One of the aims of the present invention is to provide a more reliable humidity sensor.

For this, the present invention consists of a humidity sensor comprising a silicon base plate, on which several intermetallic dielectric layers, each of which provided with a metallic zone, and a metal layer are arranged, wherein said metal layer is etched to form two electrodes, each comprising an armature provided with a multiplicity of arms, wherein these armatures are mounted so that the arms of each armature are interlaced to have arms positioned to face one another, characterised in that said sensor additionally comprises an active layer deposited directly onto the base plate to be interposed between said base plate and the first intermetallic dielectric layer, in which a temperature detector is arranged, wherein this temperature detector supplies a signal representing the temperature.

In a first advantageous embodiment the temperature module comprises a temperature detector having two bipolar transistors in parallel, each transistor is connected by its base and its collector to earth and by its emitter to a current source connected to a power supply.

In a second advantageous embodiment the temperature module comprises a temperature detector having one bipolar transistor in parallel connected by its base and its collector to earth and by its emitter to a current source connected to a power supply and a voltage source supplying a reference voltage.

In a third advantageous embodiment each transistor comprises a p-type silicon substrate, an n-type zone formed on the p-type substrate, a silicon dioxide layer being deposited on this p-type silicon substrate and locally etched, so that metal forming connection pads for the base, the emitter and the collector of said transistor can be deposited there, wherein p+-type zones are arranged below each metal pad forming the collector and the emitter, whereas an n+ zone is arranged below the pad of the base.

In a fourth advantageous embodiment for each bipolar transistor the base-emitter voltage at the connection point between said transistor and the current source is extracted to be directed to a differential amplifier, wherein said differential amplifier realises the difference of the base-emitter voltages of the two transistors to supply a voltage representing the temperature.

In another advantageous embodiment the base-emitter voltage at the connection point between said transistor and the current source is extracted to be directed to a differential amplifier, wherein said differential amplifier realises the difference between the base-emitter voltage and the reference voltage to supply a voltage representing the temperature.

In another advantageous embodiment the differential amplifier is arranged to be connected to an analog to digital converter that supplies a signal to a microcontroller via a digital interface.

In another advantageous embodiment the sensor additionally comprises a heating element.

In another advantageous embodiment the heating element is arranged at the level of a layer interposed between the active layer and the first intermetallic dielectric layer.

The invention also relates to a humidity sensor comprising a silicon base plate, on which at least a plurality of intermetallic dielectric layers, each of which provided with a metallic zone, and a metal layer are arranged, wherein said metal layer is etched to form two electrodes, each comprising an armature provided with a multiplicity of arms, wherein these armatures are mounted so that the arms of each armature are interlaced to have arms positioned to face one another, characterised in that said sensor additionally comprises an active layer interposed between the base plate and the first intermetallic dielectric layer and a layer interposed between the active layer and the first intermetallic dielectric layer, in which a heating element is arranged.

In another advantageous embodiment said heating element comprises a polycrystalline silicon layer forming a resistor connected to a metallic zone of at least one intermetallic dielectric layer via connection pads.

In another advantageous embodiment said heating element comprises a plurality of resistors arranged in parallel, wherein each resistor is connected by one of its terminals to earth and by another of its terminals to a control transistor, which is itself connected to a supply voltage, wherein said control transistor receives a signal to allow or prevent the passage of the current into the resistor.

In another advantageous embodiment all the transistors are controlled by the same control signal.

In another advantageous embodiment all the transistors are controlled in a different manner from each other.

BRIEF DESCRIPTION OF THE FIGURES

The aims, advantages and features of the invention will become clearer from the following detailed description of at least one embodiment of the invention given solely as non-restrictive example and illustrated by the attached drawings.

DETAILED DESCRIPTION

Figure 1:
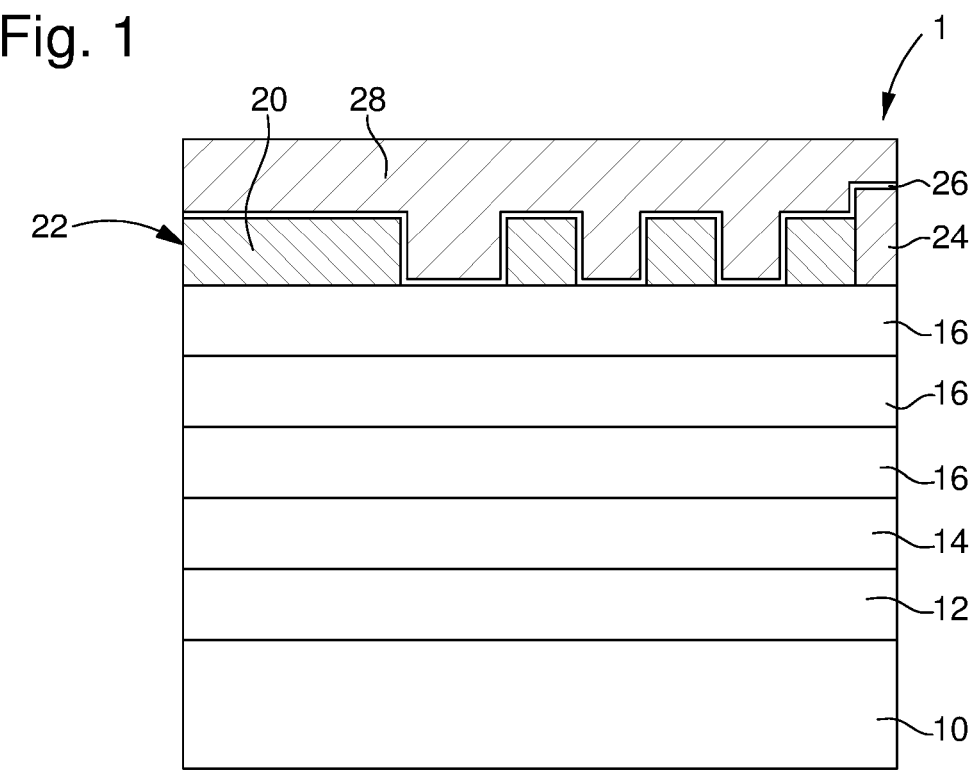
FIGS. 1 to 2 schematically show an embodiment of the humidity sensor according to the invention.

FIG. 1 shows a humidity sensor 1 according to an embodiment of the invention. Such a sensor comprises a silicon base plate 10 called a wafer. This base plate 10 serves as substrate for said sensor and a first step consists of providing this base plate 10.

Different layers are deposited successively on this substrate in a second step. A first layer 12 is deposited. This layer comprises a so-called active zone and a silicon dioxide zone.

On top of this first layer an inter-level dielectric (ILD) layer 14 is deposited.

Then, a plurality of intermetallic dielectric (IMD) layers 16 are deposited. These layers 16, preferably three in number (IMD1, IMD2 and IMD3), are superposed and each comprises metallic zones 18 for electric conduction. These metallic zones 18 may be connected together by VIA type connectors 18a.

On top of these intermetallic dielectric layers a conductive layer 20 is formed that serves as interdigitated comb, wherein this layer is deposited during the second step and can be made from aluminium, as evident in FIG. 1. This second step is a step known to the person skilled in the art.

This aluminium layer is etched during a third step to form said comb. An interdigital comb is generally formed by two electrodes 22, each having an armature provided with a multiplicity of arms. These armatures are mounted so that the arms of each armature are interlaced.

Once the comb has been formed, a fourth step consists of covering the whole assembly with a passivation layer 24.

Once this passivation layer has been etched, an opening step or fifth step is conducted. The opening step occurs during the same phase, i.e. following on from the preceding steps.

This opening step consists of firstly removing the passivation layer at the level of the interdigitated comb forming the sensor by means of etching.

Once this fifth step has been performed, a sixth step consisting of depositing a protection layer 26 (capping layer or covering layer, humidity barrier etc.) is conducted. In fact, there is a risk of corrosion of the aluminium of the electrodes in contact with the polyimide, which is a protection layer deposited subsequently, and the aluminium diffusing into the polyimide. In the case of our solution this protection layer is made from oxynitride (SiONx) with a thickness of 20 nm±2 nm.

In a seventh step the passivation layer at the level of the contact areas is open, wherein these contact areas are formed on the metal layer 20 deposited on the last intermetallic dielectric layer 16. The contact areas thus cleared allow the contact means to be placed there.

In the following steps a polyimide layer 28 is deposited and contact means are arranged.

Advantageously according to the invention the humidity sensor additionally comprises a temperature module 200. Such a temperature module 200 firstly comprises a temperature detector 210. In fact, a humidity sensor is sensitive to temperature so that the information supplied by said sensor varies according to the temperature. The temperature detector 210 used allows the temperature to be measured and temperature information to be supplied. This information may be sent to a microcontroller arranged on the same base plate or on another base plate. This information is used by the microcontroller 300.

In fact, the microcontroller 300 could comprise a storage zone, in which a correspondence table is stored, or manage a predefined transfer function. The correspondence table enables the drift of the humidity sensor to be known for a given temperature and thus the humidity information supplied to be corrected.

Expediently, the temperature detector 210 is arranged on the same base plate of the humidity sensor 1. More specifically, this temperature detector 210 is composed of a plurality of bipolar transistors. A bipolar transistor consists of two p-n junctions to form an npn or pnp structure. In a pnp bipolar transistor, in which the base is connected to the n zone, whereas the emitter and the collector are connected to a p zone.

At the level of the humidity sensor as described above, bipolar transistors are arranged at the level of the first layer 12 comprising a so-called active zone and a silicon dioxide zone.

Figure 2:
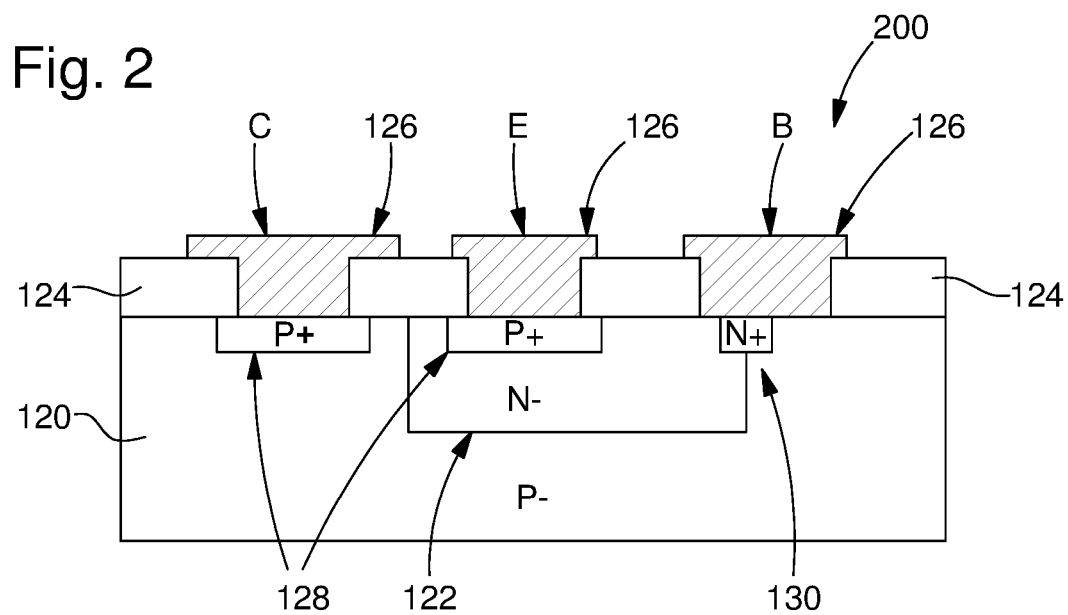

The active zone is configured so as to be provided in the form of a p-type silicon substrate 120, in which bipolar transistors are arranged as evident in FIG. 2. These transistors have an n-type zone 122 configured on the p-type substrate. A silicon dioxide layer 124 is deposited onto this p-type silicon substrate and this layer is etched locally so that metal can be deposited there to form metal parts 126 for the base, the emitter and the collector. For the collector and the emitter p+-type diffusions are arranged under each metal pad, whereas an n+ anchor 130 is arranged under the base pad.

Such a temperature detector 210 may be configured in several different ways.

Figure 3A:
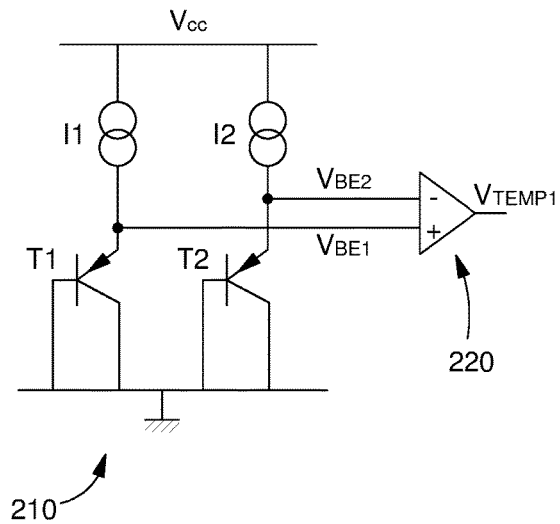
FIGS. 3a, 4a show embodiments of the temperature detector of the humidity sensor according to the invention.
Figure 4A:
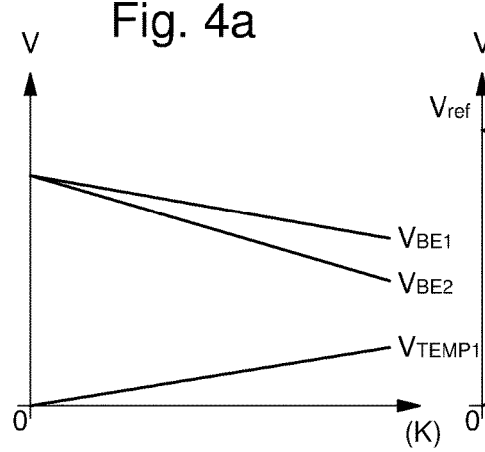

In a first embodiment evident from FIGS. 3a and 4a this consists of two pnp-type bipolar transistors referred to as T1 and T2 set in parallel, wherein each transistor T1 and T2 has its base and its collector connected to earth, whereas the emitter is connected to a current source I1, I2. For each branch the voltage at the connection point of the current source and the emitter, referred to as $V_{BE}$, is extracted to be directed to a differential amplifier 220. Transistor T1 has a base-emitter voltage referred to as $V_{BE1}$, whereas transistor T2 has a base-emitter voltage referred to as $V_{BE2}$.

In fact, such a pnp transistor has a base-emitter voltage $V_{BE}$ having a voltage characteristic as a function of the temperature in degrees Kelvin, wherein this voltage $V_{BE}$ amounts to a forbidden band voltage $V_{BG}$ at temperature T=0K° and the value of this voltage $V_{BE}$ decreases with the temperature.

In the present case the two voltages $V_{BE1}$ and $V_{BE2}$ are arranged to be different: if the currents are identical, then the transistors have different dimensions (emitter surface), but if the dimensions (emitter surface) are equal, the currents are different. In practice, to form different surfaces with well defined relations identical transistors in parallel are used. The two voltages $V_{BE1}$ and $V_{BE2}$ are passed into a circuit performing the difference between these voltages such as a differential amplifier 220 to obtain a resulting voltage $V_{TEMP1}=V_{BE1}-V_{BE2}$. This voltage $V_{TEMP1}$ has the feature of linearly increasing with temperature on a voltage-temperature diagram.

When this diagram is converted into degrees Celsius, an offset is established at T=0° C. and it is therefore possible to have a resulting voltage $V_{TEMP1}$ as a function of the temperature.

Figure 3B:
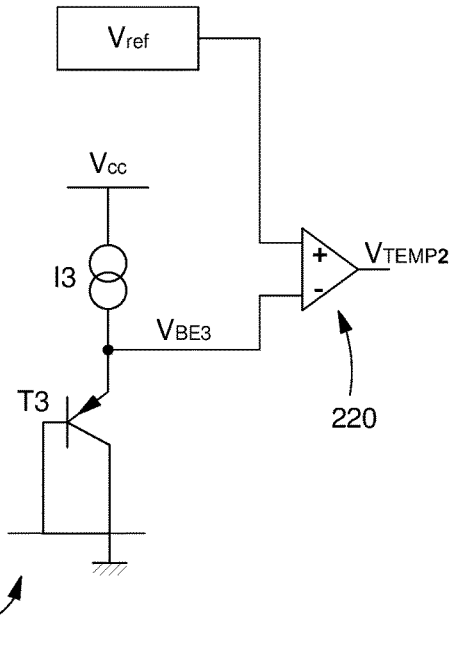
FIGS. 3b, 4b show diagrams of voltages associated with the embodiments of the temperature detector of the humidity sensor according to the invention.
Figure 4B:
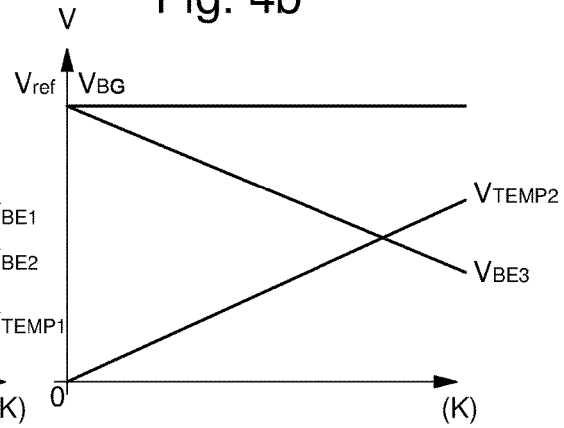

In a second embodiment evident in FIGS. 3b and 4b the temperature detector 210 comprises a pnp-type bipolar transistor referred to as T3 having its base and its collector connected to earth, whereas the emitter is connected to a current source I3. The voltage at the connection point of the current source I3 and the emitter, referred to as $V_{BE3}$, is extracted to be directed to a differential amplifier 220. The other terminal of the differential amplifier 220 is connected to a source of reference voltage $V_{ref}$, the value of which is a value of forbidden band voltage $V_{BG}$ amounting to about 1.285V. Voltage $V_{BG}$ and voltage $V_{BE3}$ are thus directed to a differential amplifier 220, which will supply a resulting voltage $V_{TEMP2}=V_{BG}-V_{BE3}$.

This voltage $V_{TEMP2}$ has the feature of linearly increasing with temperature on a voltage-temperature diagram. When this diagram is converted into degrees Celsius, an offset is established at T=0° C. and it is therefore possible to have a resulting voltage $V_{TEMP2}$ as a function of the temperature.

It is noted that this second procedure has an advantage in terms of precision. In fact, the comparison between the voltage $V_{BE3}$ and a reference voltage $V_{BG}$ results in a resulting voltage $V_{TEMP2}$ having a steeper slope than the resulting voltage $V_{TEMP1}$. This slope difference indicates an offset difference at T=0° C. between $V_{TEMP2}$ and $V_{TEMP1}$, the offset of $V_{TEMP2}$ being much more significant than the offset of $V_{TEMP1}$.

This difference in offset and in slope causes the second manner of assembly to be more precise, since, given that the slope (in mV/° C.) is higher, each temperature rise corresponds to a higher rise in voltage, which becomes more easily detectable. With the first manner of assembly a lower slope indicates that each rise in temperature corresponds to a lesser rise in voltage. This lesser rise is therefore more difficult to detect and indicates the use of a gain stage for the detection of the voltage variation and therefore the temperature variation. A gain stage can in fact lead to a higher noise level or the occurrence of saturations that degrade the signal.

Figure 5:
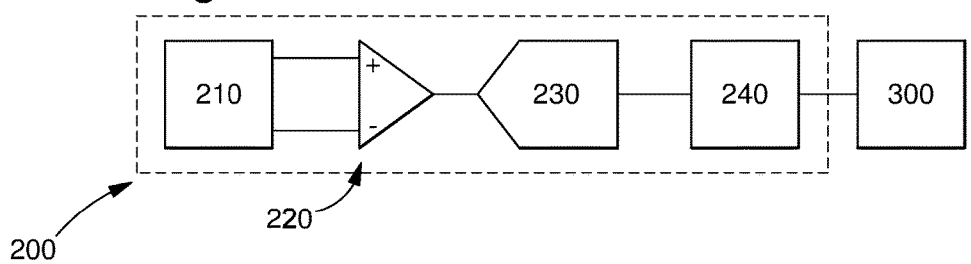
FIG. 5 shows a temperature module of the humidity sensor according to the invention.

The resulting voltage $V_{TEMP1}$ or $V_{TEMP2}$ is directed into a processing circuit evident from FIG. 5 comprising an analog to digital converter 230, an SPI or I$_2$C type digital interface 240 in order to have an electrical signal representing the temperature, which is then supplied to a microprocessor 300, which will use it to conduct a thermal compensation on said humidity sensor so that the drift because of the temperature is compensated. This compensation is performed using a transfer function.

The differential amplifier 220 may, of course, be integrated directly into the analog/digital converter 230.

In an advantageous variant the humidity sensor according to the present invention is provided with a heating element 30. Such a heating element is used to assure reconditioning, i.e. removing the humidity present during the production process, removing the condensation or improving the hysteresis and the recovery time of the humidity sensor.

A second way of using this heating element 30 is to use it following exposure to an excessive humidity. In actual fact, exposure of the polyimide layer to an extreme humidity can impair the proper operation of the humidity sensor 1, as the polyimide layer covers the metallic structure forming said sensor. The heating element 30 is thus used to accelerate the evacuation of this excess humidity from the polyimide layer. For this, the heating element 30 is activated in order to increase the temperature of the sensor and to dry the polyimide layer.

Figure 6:
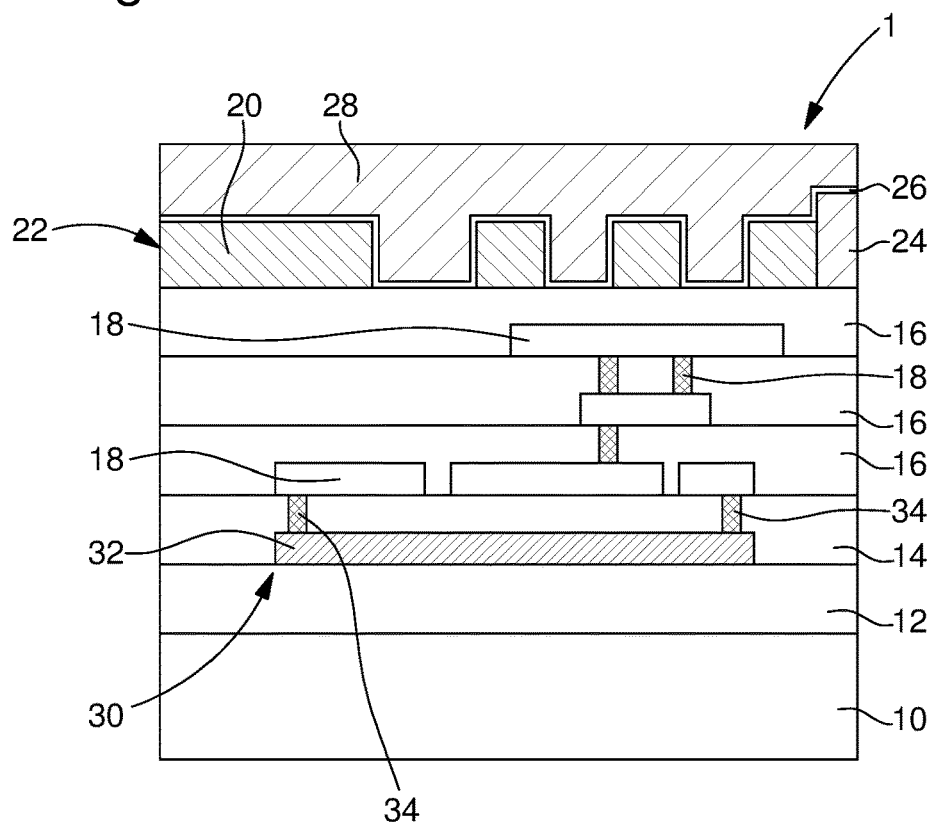
FIGS. 6 and 7 show a heating element of the humidity sensor according to the invention.

A heating element 30, evident in FIG. 6, that is used is a resistor, and more specifically a polycrystalline resistor 32. Such a polycrystalline resistor 32 consists of a layer of polycrystalline silicon. This polycrystalline silicon layer is arranged at the level of the inter-level dielectric (ILD) layer 14 deposited on the first so-called active layer 12. To enable the heat produced by the polycrystalline resistor to diffuse, the inter-level dielectric (ILD) layer 14 is provided with metal connections 34. These metal connections extend in at least one of the intermetallic dielectric (IMD) layers 16 to be connected to the metallic zone of this intermetallic dielectric (IMD) layer 16. A current in the order of 40 mA is directed into the polycrystalline silicon layer to activate the heating function.

Figure 7:
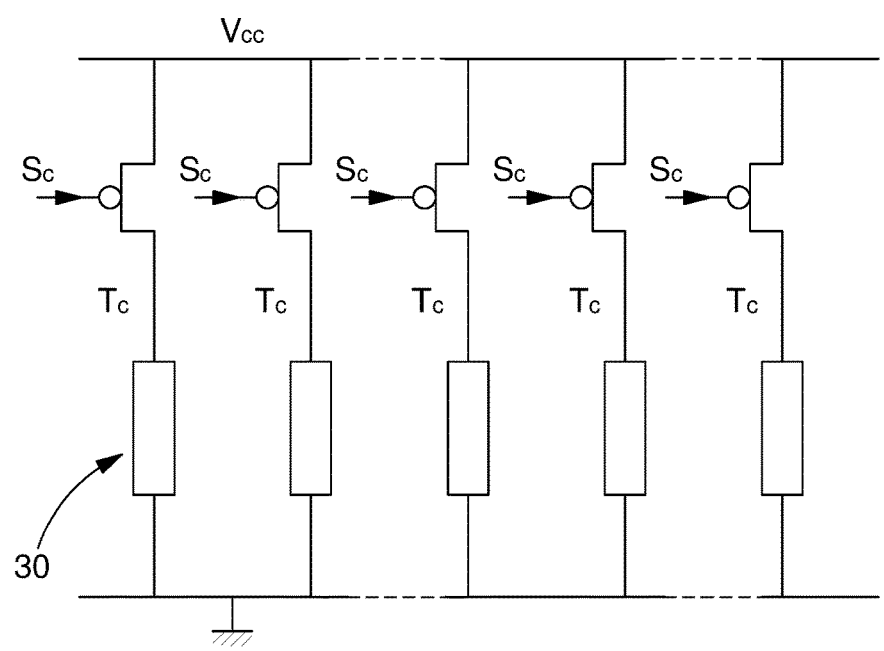

This heating element 30 evident in FIG. 7 may be configured in the form of a plurality of modules, each of which comprising a resistor and each resistor being connected to a control transistor $T_C$ that receives a control signal Sc, wherein the modules are connected in parallel. This configuration allows a good distribution of heat over the entire sensor.

It is additionally conceivable that the humidity sensor 1 has the heating element 30 without the temperature module 200 or vice versa.

It will be understood that various modifications and/or improvements and/or combinations evident to a person skilled in the art can be applied to the different embodiments of the invention outlined above without departing from the framework of the invention defined in the attached claims.

The invention claimed is:

1. A humidity sensor, comprising:
   a silicon base plate, on which a stack of a plurality of intermetallic dielectric layers, each of which is provided with a metallic zone, and a metal layer are disposed,
   wherein the metal layer is etched to form two electrodes, each comprising an armature provided with a plurality of arms, the armatures being mounted so that the arms of said each armature are interlaced such that the arms are positioned to face one another;
   an active layer, deposited directly onto the silicon base plate and being interposed between the silicon base plate and a first intermetallic dielectric layer of said stack of the plurality of intermetallic dielectric layers, the first intermetallic dielectric layer being disposed closest to the silicon base plate among the stack of the plurality of intermetallic dielectric layers, wherein a temperature module is disposed in the active layer, the temperature module supplying a signal representing a temperature, the temperature module comprising a temperature detector having:
   a bipolar transistor connected by a base and a collector thereof to earth,
   a current source, one terminal of which is connected to a power supply and another terminal of which is connected to an emitter of the bipolar transistor,
   a voltage source supplying a reference voltage, and
   a differential amplifier, wherein a base-emitter voltage at a connection point between the bipolar transistor and the current source is extracted to be directed to the differential amplifier, the differential amplifier providing a difference between the base-emitter voltage and the reference voltage to supply a voltage representing the temperature;
   an interlevel dielectric layer deposited directly on the active layer and being disposed between the active layer and the first intermetallic dielectric layer; and
   a heating element deposited on the active layer and being disposed within the interlevel dielectric layer.

2. The humidity sensor according to claim 1,
   wherein the bipolar transistor further comprises a p-type silicon substrate, an n-type zone formed on the p-type silicon substrate, a silicon dioxide layer deposited onto the p-type silicon substrate and locally etched such that metal forms connection pads for the base, the emitter, and the collector of the bipolar transistor configured to be deposited there,
   wherein p+-type zones are disposed below each connection pad forming the collector and the emitter, and
   wherein an n+ anchor is disposed below the connection pad of the base.

3. The humidity sensor according to claim 1, wherein the differential amplifier is configured to be connected to an analog-to-digital converter that supplies another signal to a microcontroller via a digital interface.

4. A humidity sensor, comprising:
   a silicon base plate, on which at least a stack of a plurality of intermetallic dielectric layers, each of which is provided with a metallic zone, and a metal layer are disposed,
   wherein the metal layer is etched to form two electrodes, each comprising an armature provided with a plurality of arms, the armatures being mounted so that the arms of said each armature are interlaced such that the arms are positioned to face one another;
   an active layer interposed between the silicon base plate and a first intermetallic dielectric layer of said stack of the plurality of intermetallic dielectric layers, the first intermetallic dielectric layer being disposed closest to the silicon base plate among the stack of the plurality of intermetallic dielectric layers;
   an interlevel dielectric layer deposited directly on the active layer and being interposed between the active layer and the first intermetallic dielectric layer; and
   a heating element deposited on the active layer and being disposed within the interlevel dielectric layer.

5. The humidity sensor according to claim 4, wherein the heating element comprises a polycrystalline silicon layer forming a resistor connected to a metallic zone of at least one intermetallic dielectric layer of said plurality of intermetallic dielectric layers via connection pads.

6. The humidity sensor according to claim 5,
   wherein the heating element further comprises a plurality of resistors arranged in parallel,
   wherein each resistor of the plurality of resistors is connected by one terminal to earth and by another terminal to a control transistor, the control transistor being connected to a supply voltage, and
   wherein the control transistor receives a signal to allow or to prevent passage of current into a resistor of the plurality of resistors.

* * * * *